United States Patent [19]

Treybig

[11] Patent Number: 4,961,867

[45] Date of Patent: Oct. 9, 1990

[54] PROCESS FOR PREVENTING CORROSION OF METALS BY CONTACTING THEM WITH COMPOSITIONS PREPARED FROM AMINO SUBSTITUTED PYRAZINES AND CARBOXYLIC ACIDS CARBOXYLIC ACID ANHYDRIDES, CARBOXYLIC ACID, ESTERS OR CARBOXYLIC ACID HALIDES

[75] Inventor: Duane S. Treybig, Lake Jackson, Tex.

[73] Assignee: The Dow Chemical Company, Midland, Mich.

[21] Appl. No.: 310,798

[22] Filed: Feb. 14, 1989

Related U.S. Application Data

[60] Division of Ser. No. 176,901, Apr. 4, 1988, Pat. No. 4,861,884, which is a continuation-in-part of Ser. No. 787,586, Oct. 15, 1985, abandoned.

[51] Int. Cl.$^5$ .............................................. C23F 11/14
[52] U.S. Cl. .................................. 252/8.555; 252/390; 544/336; 544/357; 544/408; 544/409

[58] Field of Search ............................... 252/8.555, 390

[56] References Cited

U.S. PATENT DOCUMENTS

| | | | |
|---|---|---|---|
| 4,212,764 | 7/1980 | Quinlan | 252/392 X |
| 4,251,384 | 2/1981 | Rooney | 252/147 X |
| 4,329,381 | 5/1982 | Eschwey et al. | 427/386 X |
| 4,676,834 | 2/1986 | Treybig | 106/14.15 X |
| 4,725,373 | 2/1988 | Treybig et al. | 252/8.555 |
| 4,740,320 | 4/1988 | Treybig et al. | 252/8.555 |
| 4,762,627 | 8/1988 | Martinez et al. | 252/8.555 |

*Primary Examiner*—John F. Terapane
*Assistant Examiner*—Chhaya Sayala

[57] ABSTRACT

Novel compositions are prepared from (1) amino substituted pyrazine compounds such as pyrazinamine and (2) at least one of (a) a carboxylic acid, (b) carboxylic acid anhydride, (c) carboxylic acid ester or (d) combination thereof, such as tall oil fatty acid, and (3) optionally in the presence of sodium hydride. These novel compositions are useful as oil and gas well corrosion inhibitors.

15 Claims, No Drawings

PROCESS FOR PREVENTING CORROSION OF METALS BY CONTACTING THEM WITH COMPOSITIONS PREPARED FROM AMINO SUBSTITUTED PYRAZINES AND CARBOXYLIC ACIDS CARBOXYLIC ACID ANHYDRIDES, CARBOXYLIC ACID, ESTERS OR CARBOXYLIC ACID HALIDES

CROSS REFERENCE TO RELATED APPLICATION

This application is a division of application Ser. No. 07/176,901 now U.S. Pat. No. 4,861,884 filed Apr. 4, 1988 which is a continuation-in-part of application Ser. No. 787,586 filed Oct. 15, 1985, now abandoned.

BACKGROUND OF THE INVENTION

The present invention pertains to novel compositions prepared by reacting amino substituted pyrazines with carboxylic acids, carboxylic acid anhydride, carboxylic acid esters or carboxylic acid halides.

During the drilling and servicing of oil and gas wells, the metal tools and equipment associated therewith are susceptible to corrosion. It is therefore highly desirable to have corrosion inhibitors for the protection of these metal tools and equipment. The present invention provides corrosion inhibitors for use at both low and high temperatures. The deeper the wells, the higher the temperature; therefore there is a need for inhibitors suitable for use at both low and high temperatures.

SUMMARY OF THE INVENTION

One aspect of the present invention concerns new compositions of matter which comprise the reaction product of
(A) at least one pyrazine compound having at least one substituent —NH$_2$ and/or —NH— group;
(B) at least one of the following:
 (1) at least one carboxylic acid;
 (2) at least one carboxylic acid anhydride;
 (3) at least one carboxylic acid halide;
 (4) at least one ester of a carboxylic acid; or
 (5) any combination of (1), (2), (3), and (4); and
(C) optionally in the presence of sodium hydride; and wherein components (A) and (B) are present in quantities which provide a ratio of

groups to —NH$_2$ and/or —NH— groups of from about 0.25:1 to about 1.2:1, preferably from about 0.75:1 to about 1.2:1, most preferably from about 0.9:1 to about 1.1:1 and component (C) is present in quantities which provide a ratio of sodium hydride to —NH$_2$ and/or —NH— groups of from about 0:1 to about 1.5:1, preferably from about 0.75:1 to about 1.2:1, most preferably from about 0.9:1 to about 1.2:1.

Another aspect of the present invention pertains to a process for preventing or reducing the corrosion of a metal composition in contact with down hole well fluids, which process comprises contacting the surface of said metal composition with an effective amount of the aforementioned novel compositions.

DETAILED DESCRIPTION OF THE INVENTION

The corrosion inhibitors of the present invention are prepared by reacting the amino substituted pyrazine compound or mixture of such compounds with a carboxylic acid, or a carboxylic acid anhydride, or a carboxylic acid ester or a carboxylic acid halide or combination thereof at a temperature of from about 0° C. to about 300° C. for a time sufficient to complete the reaction. The preferred temperature for the reaction of an amino substituted pyrazine compound with a carboxylic acid halide is from about 0° C. to about 200° C., most preferably from about 50° C. to about 150° C. The preferred temperature for the reaction of an amino substituted pyrazine compound with a carboxylic acid is from about 60° C. to about 190° C., most preferably from about 60° C. to about 150° C. The preferred temperature for the reaction of an amino substituted pyrazine compound with a carboxylic acid anhydride, carboxylic acid ester or combination thereof is from about 150° C. to about 250° C., most preferably from about 180° C. to about 230° C. The reaction time depends on whether a carboxylic acid, or a carboxylic acid anhydride, or a carboxylic acid ester or a carboxylic acid halide is reacted with the amino substituted pyrazine compound. The reaction of a carboxylic acid halide with an amino substituted pyrazine compound usually requires from about ten minutes (600 s) to about 4 hours (230,400 s), preferably from about ten minutes (600 s) to about 1 hour (3600 s), most preferably from about ten minutes (600 s) to about 30 minutes (1800 s) for completion. The reaction of a carboxylic acid, carboxylic acid anhydride or carboxylic acid ester with an amino substituted pyrazine compound usually requires from about 1 hour (3600 s) to about 48 hours (172,800 s), preferably from about 1 hour (3600 s) to about 24 hours (86,400 s), most preferably from about 1 hour (3600 s) to about 10 hours (36,000 s) for completion. These reactions can be carried out under reduced pressure if desired.

When an amino substituted pyrazine is reacted with a carboxylic acid anhydride or carboxylic acid halide, an amide is the predominant product; however when an amino substituted pyrazine is reacted with a carboxylic acid, the predominant product is a salt of the carboxylic acid and the amino pyrazine compound. When an amino substituted pyrazine is reacted with a carboxylic acid ester, no appreciable concentration of amide or salt is formed.

Pyrazinamine is not very reactive with a carboxylic acid or carboxylic acid ester because the amino group of pyrazinamine is not very basic. Sodium hydride was reacted with pyrazinamine to deprotonate an external amine hydrogen and make pyrazinamine more reactive with carboxylic acids or carboxylic acid esters. The corrosion protection of the product from the reaction of pyrazinamine with a carboxylic acid ester in the presence of sodium hydride was improved over the corrosion protection provided by the product from the reaction of pyrazinamine with a carboxylic acid ester, alone. The predominant products formed from the reaction of pyrazinamine with a carboxylic acid ester in the presence of sodium hydride were an amide and apparently a salt of sodium and a carboxylic acid. The corrosion protection of the product from the reaction of pyrazinamine with a carboxylic acid in the presence of sodium hydride was similar to the protection provided by the product from the reaction of pyrazinamine with a carboxylic acid alone.

Suitable amino-substituted pyrazine compounds which can be employed herein include those represented by the formula

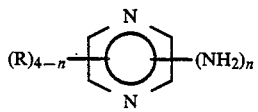

(I)

wherein each R is independently hydrogen, a hydrocarbyl group having from 1 to about 20, preferably from about 1 to about 10, most preferably from about 1 to about 4 carbon atoms; a halogen atom, an oxygen atom, an —O—, —OH, —OR, —SH or —SR group and n has a value from 1 to 4.

The term hydrocarbyl as employed herein means any aliphatic cycloaliphatic, aromatic, aryl substituted aliphatic or aliphatic substituted aromatic groups.

Particularly suitable such amino-substituted pyrazine compounds include, for example, pyrazinamine (aminopyrazine), 3-chloropyrazinamine, 5-chloropyrazinamine, 6-chloropyrazinamine, pyrazinamine-1-oxide, 3-amino-2(1H)pyrazinethione, 2,3-pyrazinediamine, 2,6-pyrazinediamine, 5,6-dichloro-2,3-pyrazinediamine, 3,5-dichloro-2,6-pyrazinediamine, 2,3,5-pyrazinetriamine, pyrazinetetramine, mixtures thereof and the like.

Suitable carboxylic acids which can be employed herein include those represented by the following formulas

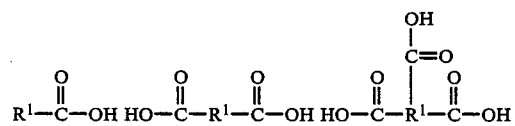

(II)

wherein $R^1$ is a hydrocarbyl group or a sulfur, halogen, nitro or hydroxyl substituted hydrocarbyl group having from about 1 to about 72 carbon atoms, preferably from about 10 to about 36 carbon atoms, most preferably an alkyl group having from about 12 to about 24 carbon atoms.

Particularly suitable carboxylic acids which can be employed herein include, for example, heptanoic acid, octanoic acid, nonanoic acid, decanoic acid, undecanoic acid, dodecanoic acid (lauric acid), tridecanoic acid, tetradecanoic acid (myristic acid), pentadecanoic acid, hexadecanoic acid (palmitic acid), heptadecanoic acid, octadecanoic acid (stearic acid), nonadecanoic acid, eicosanoic acid, heneicosanoic acid, docosanoic acid, tricosanoic acid, tetracosanoic acid, tricontanoic acid, 2-propylpentanoic acid, 2-ethylhexanoic acid, 5-methyl-2-(5-methylhexyl)decanoic acid, 8-methylheptadecanoic acid, 3-methylpentadecanoic acid, 2-octenoic acid, trans-9-octadecenoic acid (elaidic acid), 12-octadecenoic acid, 9,12-octadecadienoic acid (linoleic acid), 13-docosenoic acid (erucic acid), 2,4-hexadienoic acid, 9,12,15-octadecatrienoic acid (linolenic acid), 5,8,11,14-eicosatetraenoic acid (arachidonic acid), 3,5-tetradecadienoic acid, 6-hexadecenoic acid, 3-hexyl-3-decenoic acid, 5,8-hexadecadienoic acid, 2-hydroxy-1,2,3-nonadecanetricarboxylic acid (agaricic acid), 11-bromoundecanoic acid, 2-bromohexadecanoic acid, 12-nitrododecanoic acid, 16-hydroxyhexadecanoic acid, 4-hydroxyoctadecanoic acid, 12-hydroxyoctadecanoic acid (DL-12-hydroxystearic acid), 4,4'-dithiobisbutanoic acid, decanedioic acid (sebacic acid), undecanedioic acid, dodecanedioic acid, tridecanedioic acid, tetradecanedioic acid, hexadecanedioic acid, trans-4-pentylcyclohexanecarboxylic acid, cyclohexane- butanoic acid, cyclohexanehexanoic acid, 3-methyltricyclo[3.3.1.1$^{3,7}$]decane-1-acetic acid, benzenebutanoic acid, benzenehexanoic acid, 11-phenoxyundecanoic acid, tall oil fatty acids, rosin acids, dimer acids such as Westvaco Diacid 1550, Empol 1010 dimer acid and Empol 1016 dimer acid, trimer acids such as Empol 1040 trimer acid, polycarboxylic acids such as Empol 1052 polybasic acid, mixtures thereof and the like. Other suitable carboxylic acids are disclosed in U.S. Pat. No. 4,339,349, which is incorporated herein by reference.

Suitable carboxylic acid anhydrides which can be employed herein include those represented by the following formula

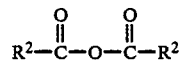

(III)

wherein each $R^2$ is independently a hydrocarbyl group or a sulfur, halogen, nitro or hydroxyl substituted hydrocarbyl group having from about 1 to about 72 carbon atoms, preferably from about 10 to about 36 carbon atoms, most preferably an alkyl group having from about 12 to about 24 carbon atoms.

Particularly suitable carboxylic acid anhydrides which can be employed herein include, for example, heptanoic acid anhydride, decanoic acid anhydride, dodecanoic acid anhydride, tetradecanoic acid anhydride, pentadecanoic acid anhydride, hexadecanoic acid anhydride, heptadecanoic acid anhydride, octadecanoic acid anhydride, dodecanoic acid anhydride with tetradecanoic acid, heptadecanoic acid anhydride with octadecanoic acid mixtures thereof and the like.

Suitable esters of carboxylic acids which can be employed herein include those represented by the following formulas

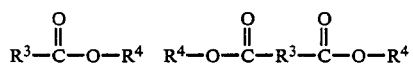

(IV)

wherein each $R^3$ and $R^4$ is independently a hydrocarbyl group or a sulfur, halogen, nitro or hydroxyl substituted hydrocarbyl group having from about 1 to about 72 carbon atoms, preferably from about 10 to about 36 carbon atoms, most preferably an alkyl group having from about 12 to about 24 carbon atoms.

Particularly suitable carboxylic acid esters which can be employed herein include, for example, heptanoic acid methyl ester (methyl caprylate), decanoic acid ethyl ester (ethyl caprate), undecanoic acid ethyl ester (ethyl undecanoate), decanoic acid octyl ester, dodecanoic acid methyl ester (methyl laurate), dodecanoic acid butyl ester, dodecanoic acid hexyl ester, tetradecanoic acid methyl ester (methyl myristate), tetradecanoic acid butyl ester, pentadecanoic acid methyl ester (methyl pentadecanoate), pentadecanoic acid-1-methylethyl ester, hexadecanoic acid methyl ester (methyl palmitate), hexadecanoic acid ethyl ester, octadecanoic acid methyl ester (methyl stearate), octadecanoic acid ethyl ester (ethyl stearate), eicosanoic acid methyl ester (methyl eicosanoate), docosanoic acid methyl ester (methyl docosanoate), tricontanoic acid ethyl ester (ethyl tricontanoate), 5-pentadecenoic acid methyl ester, 2-tetradecenoic acid ethyl ester, 14-methyl-8-hexadecenoic acid methyl ester, 2-hexadecenoic acid ethyl ester, decanedioic acid dimethyl ester, tridecanedioic acid dimethyl ester, tetradecanedioic acid diethyl ester, trans-11-tetradecen-1-yl acetate, tripropylene glycol diacrylate, cyclohexanepropanoic acid ethyl ester, mixtures thereof and the like.

Suitable carboxylic acid halides which can be employed herein include those represented by the following formulas

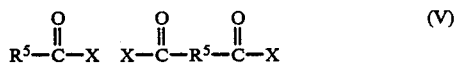

wherein each $R^5$ is independently a hydrocarbyl group or a sulfur, halogen, nitro or hydroxyl substituted hydrocarbyl group having from about 1 to about 72 carbon atoms, preferably from about 10 to about 36 carbon atoms, most preferably an alkyl group having from about 12 to about 24 carbon atoms.

Particularly suitable carboxylic acid halides which can be employed herein include, for example, nonanoyl chloride, decanoyl chloride, 2-hexyldecanoyl chloride, 2-butyldecanoyl chloride, undecanoyl chloride, dodecanoyl chloride (lauroyl chloride), 2,2-dimethyldodecanoyl chloride, 2-ethyldodecanoyl chloride, 2,4,6-trimethyl-2-(2-methylpropyl)-heptanoyl chloride, tetradecanoyl chloride (myristoyl chloride), hexadecanoyl chloride (palmitoyl chloride), octadecanoyl chloride (stearoyl chloride), 10-undecenoyl chloride, 9-octadecenoyl chloride, 10-octadecenoyl chloride, decanedioyl chloride, tricyclo[3.3.1.1$^{3,7}$]decane-1-carbonyl chloride, mixtures thereof and the like.

If desired, the compositions of the present invention can be prepared in the presence of one or more solvents. Suitable such solvents include, for example, cyclic ethers, halogenated solvents, amides, furans, hydrocarbons, combinations thereof and the like.

Particularly suitable solvents include, for example, tetrahydrofuran, methylene chloride, dimethylformamide, N,N-dimethylacetamide, dioxane, N,N-dimethylmethoxyacetamide, N-methyl-pyrrolidinone, benzene, toluene, combinations thereof and the like.

The compositions of the present invention can be employed as a corrosion inhibitor as are conventional corrosion inhibitors. Generally, the product can be employed in corrosion inhibitor formulations as are known in the art. For example, the product can be dispersed or dissolved in a suitable carrier liquid or solvent such as water, alcohols, aromatic and aliphatic hydrocarbons, and the like, or mixtures thereof. Other additives include demulsifiers, water wetting agents, surfactants, viscosifiers, commingled gases, defoamers, other corrosion inhibitors such as polymeric materials and salts, organic and inorganic acids, iron control agents, sequestering and/or chelating agents, phosphates, quaternaries, amine salts, and the like. For example, surface active agents are used to assure complete dispersion of active ingredients throughout the corrosion inhibitor composition and thus provide a better contact of the corrosion inhibitor with the surface of the metal compound which is being protected. Some of the corrosion inhibitors of this invention form films on metal surfaces at least as readily as those known film forming corrosion inhibitors.

The corrosion inhibitor of this invention is employed in a functionally effective amount. That is, any quantity of corrosion inhibitor which will provide some degree of inhibition of corrosion is sufficient. Typical amounts of corrosion inhibitor which are employed in an oil and/or gas well treatment can range from one to about 2,000 ppm for continuous treatment or from about 200 to about 50,000 ppm for squeeze treatment, based on the weight of corrosive well fluids in contact with the metal compositions which are protected. Amounts of corrosion inhibitor in excess of 50,000 ppm can provide additional corrosion inhibition but at increased expense.

Some of the corrosion inhibitors of this invention are highly stable to high temperatures and high pressures. Typically, corrosion inhibitors are employed in applications where temperatures range from about 100° F. (37.7° C.) to in excess of about 500° F. (260° C.), depending upon the composition of the inhibitor product. Some of the corrosion inhibitors of this invention are especially useful at temperatures ranging from 100° F. (37.7° C.) to about 450° F. (232.2° C.).

The corrosion inhibitors of this invention inhibit corrosion to metal compositions used in down hole applications. The corrosion inhibitors advantageously inhibit corrosion to metal compositions at elevated temperatures exceeding 250° F. in oil and gas well applications. Useful applications include oil and/or gas well drilling, completion, workover, stimulation, transfer, processing and storage applications.

The following examples are illustrative of the present invention.

CORROSION TESTING, 175° F. (79.4° C.)

Corrosion inhibition of various samples was determined under conditions which simulate conditions that exist in oil and gas wells as follows. A brine solution containing 89.89 percent deionized water, 9.62 percent sodium chloride, 0.305 percent calcium chloride and a 0.186 percent hydrated magnesium chloride complex was prepared. This brine solution was saturated under carbon dioxide purge until a pH of 3.8 was achieved. The solution was treated with sodium persulfate to remove oxygen. The desired corrosion inhibitor was added to the solution. About 720 milliliters (ml) of this brine solution and 80 ml of kerosene (90% brine/10% kerosene) treated with sodium persulfate were charged into a 32-ounce bottle. To this charge was added enough hydrated sodium sulfide to generate a suitable amount of hydrogen sulfide (i.e., about 300 ppm hydrogen sulfide based on total fluids).

Metal coupons (12"×¼"×1/16", 304.8 mm×6.35 mm×1.59 mm) of 1020 carbon steel were degreased with an inhibited methylchloroform, acidized with 16 percent hydrochloric acid, washed and dried. Each coupon weighed about 19 g. A metal coupon was placed in the bottle containing the brine, kerosene and ingredients as previously described. The bottle was capped and acetic acid was injected into the bottle through a septum. The bottle was placed on a vertically rotating wheel held at 175° F. (79.4° C.) and the sample was rotated at 26 rpm for 24 hours (86400 s). The coupons were removed from the bottle, cleaned, washed, dried, reweighed and the percent protection afforded them by the inhibitor was calculated as the percent protection by the following formula:

$$\text{percent protection} = 100 - \frac{\text{inhibitor coupon wt. loss}}{\text{blank coupon wt. loss}} \times 100$$

The weight loss was given to the nearest whole percent. The tests wherein no inhibitor was employed were for comparative purposes and were designated as blanks.

The corrosion rates were also determined in milliinches per year (mpy) by the following formula:

$$mpy = \frac{534 \text{ (Mg Weight Loss of Coupon)}}{d \times a \times t}$$

d = density of 1020 carbon steel = 7.86 g/ml
a = surface area (in.) of metal coupons
t = test time in hours

CORROSION TESTING, 350° F. (177° C.)

The performance of 100 ppm of a corrosion inhibitor sample also was tested in a 350° F. (177° C.) wheel test containing 90 percent brine/8 percent heptane/2 percent kerosene at 2,000 psi pressure (25° C.) with 10 percent hydrogen sulfide, 10 percent carbon dioxide and 80 percent methane in a stainless steel pipe bomb. The sample was rotated at 26 rpm for 24 hours (86,400 s). Metal coupons (6"×¼"×1/16", 152.4 mm×6.35 mm×1.59 mm) of 1020 carbon steel were degreased with chlorothene, scrubbed, washed with acetone and dried before being placed in the pipe bomb. After the test, the coupons were removed from the pipe bomb, scrubbed, washed with acetone and dried. Percent protection was calculated using the same equations as in the above 175° F. corrosion test.

EXAMPLE 1

Aminopyrazine (100 g, 1.05 moles) and tall oil fatty acid (295.4 g, 1.05 moles) were weighed into a 1-liter resin kettle equipped with a reflux condenser, immersion thermometer, mechanical stirrer and Barrett trap. The reactor contents were stirred under a nitrogen atmosphere while being held at a temperature between 149° C. and 199° C. for 10 hours 37 minutes (38,220 s). On cooling to room temperature, the product was a dark reddish brown liquid. Elemental analysis showed the product consisted of 2.8% nitrogen, 74.7% carbon, 11.9% hydrogen and 11.6% oxygen. Infrared spectroscopy indicated aminopyrazine had complexed with the tall oil fatty acid or its dimer forming a salt. The presence of the salt was supported by a strong band at 1617 cm$^{-1}$ and a band at 1407 cm$^{-1}$ which are due to asymmetrical and symmetrical stretch of the carboxylate ion of the salt, respectively. A small, indeterminate concentration of the following fatty amide,

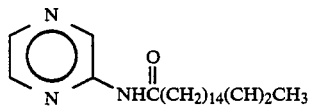

aminopyrazine, and several different tall oil fatty acid constituents were identified by electron impact mass spectroscopy. The solids were placed into a mortar, a drop of cold hydrochloric acid added and nitrogen was used to blow dry this sample. Infrared spectroscopy showed bands at 2500, 2080, 1160, 1040 and 790 cm$^{-1}$ which support the presence of aminopyrazine hydrochloride. The formation of amino pyrazine hydrochloride indicates the reaction product of 2-aminopyrazine and tall oil fatty acid is a salt or complex and not an amide. No aminopyrazine hydrochloride would have been formed if the reaction product of 2-aminopyrazine and tall oil fatty acid had been an amide. The reaction product of aminopyrazine and tall oil fatty acid was completely water soluble.

EXAMPLE 2

Aminopyrazine (100 g, (1.05 moles) and Westvaco Diacid 1550 (a liquid monocyclic C$_{21}$ dicarboxylic acid represented by the following formula,

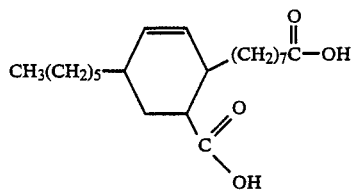

which is commercially available from Westvaco Corporation) (184.5 g, 0.53 mole) were weighed into a 500 ml resin kettle equipped with a reflux condenser, immersion thermometer, mechanical stirrer and Barrett trap. The reactor contents were stirred under a nitrogen atmosphere while being held at a temperature between 142° C. and 187° C. for 8 hours 45 minutes (31,500 s). On cooling to room temperature, the product was a dark reddish brown tacky solid. Elemental analyses of the product showed it consisted of 5.6% nitrogen, 66.8% carbon, 9.6% hydrogen and 18% oxygen. Infrared spectroscopy suggests the aminopyrazine had complexed with the diacid forming a salt. The presence of the salt was supported by a strong band at 1620 cm$^{-1}$ and a weaker band at 1408 cm$^{-1}$. Aminopyrazine was identified by electron impact mass spectroscopy. Differential scanning calorimetry indicates isomerization or decomposition of the aminopyrazine and diacid salt occurs at or above 230° C. The reaction product of aminopyrazine and Westvaco diacid 1550 was completely water soluble.

EXAMPLE 3

Aminopyrazine (50.35 grams, 0.53 mole) and tall oil fatty acid (151.41 grams, 0.54 mole) were weighed into a 250 milliliter 4-neck round bottom flask equipped with an immersion thermometer, mechanical stirrer, condenser and nitrogen purge system. The reactor contents were stirred in a nitrogen atmosphere while being held at a temperature between 233°-249° C. for 3 hours 54 minutes (14,040 s). Then the reactor contents were cooled to 188° C. and maintained between 188°-191° C. for 14 hours 18 minutes (51,480 s). Finally, the reactor contents were heated to 245° C. and maintained between 243°-249° C. for an additional 9 hours 9 minutes (32,940 s). The reactor was fitted with a stillhead and the reactor contents were subjected to distillation between 105°-149° C. and 13 mm mercury vacuum. The distillation was terminated after 39 minutes (2340 s) due to constant plugging of the vacuum lines leading from the stillhead. After cooling to room temperature, the product was a black viscous liquid. The infrared Fourier Transform spectrum of the black liquid indicated aminopyrazine had complexed with the tall oil fatty acid forming a salt. The black viscous liquid was dissolved in xylene for the corrosion inhibition tests.

EXAMPLE 4

Aminopyrazine (10.02 grams, 0.11 mole), dimethylformamide (143.07 grams), and sodium hydride (3 grams, 0.13 mole) were weighed into a reactor of the type described in Example 3. The reactor contents were stirred in a nitrogen atmosphere between 24°–37° C. for 1 hour 59 minutes (7140 s). Then tall oil fatty acid (31.02 grams, 0.11 mole) was added to the reactor. The reactor contents were heated at a temperature between 134°–151° C. for 23 hours 48 minutes (85,680 s). The reactor was fitted with a stillhead and its contents were subjected to distillation between 163°–240° C. and 7–9 mm mercury vacuum for 1 hour 43 minutes (6180 s). After cooling to room temperature, the product was a black waxy solid. The infrared Fourier Transform spectrum of the black solid showed that no free carboxylic acid was present. The absorption band at 1709 cm$^{-1}$ due to dimeric carboxylic carbonyl stretch, the band at 1401 cm$^{-1}$ from C—O—H in plane bend and the band at 1281 cm$^{-1}$ due to C—O stretch were absent. Strong absorption bands at 1563, 1443 and a weaker band at 1423 cm$^{-1}$ were present. Absorption bands at 720 cm$^{-1}$, 1470 cm$^{-1}$, 2851 cm$^{-1}$ and 2924 cm$^{-1}$ supported the presence of methylene groups. The black waxy solid was dissolved in ethanol for the corrosion inhibition tests.

EXAMPLE 5

Aminopyrazine (31.92 grams, 0.34 mole) and stearoyl chloride (101.33 grams, 0.34 mole) were weighed into a reactor of the type described in Example 3. The reactor contents were stirred while being held at a temperature between 144°–193° C. for 32 minutes (1920 s). On cooling to room temperature, the product was a gray solid that was soluble in xylene. The infrared Fourier Transform spectrum of the gray solid indicated the presence of methylene groups and a secondary amide. Absorption bands at 713 cm$^{-1}$, 1470 cm$^{-1}$, 2852 cm$^{-1}$ and 2918 cm$^{-1}$ supported the presence of methylene groups. Multiple bands between 3000 cm$^{-1}$–3303 cm$^{-1}$ were attributed to the NH stretching vibration of a secondary amide. The band at 1682 cm$^{-1}$ was assigned to the carbonyl stretching vibration (Amide I band) of a secondary amide. The band at 1556 cm$^{-1}$ was attributed to the N—H bending vibration (Amide II band) of a secondary amide. Thermogravimetric analysis showed the amide lost only 19.6% weight at 293° C. The gray solid was dissolved in xylene for the corrosion inhibition tests.

EXAMPLE 6

Aminopyrazine (47.54 grams, 0.5 mole) and methyl stearate (149.74 grams, 0.5 mole) were weighed into a reactor of the type described in Example 3. Thereactor contents were stirred while being held at a temperature between 176°–231° C. for 13 hours 18 minutes (47,880 s). After cooling to room temperature, the reactor product was a brown solid that was soluble in xylene. The infrared Fourier Transform spectrum suggested the majority of the methyl stearate had not reacted with the aminopyrazine. The brown solid was dissolved in xylene for the corrosion inhibition tests.

EXAMPLE 7

Aminopyrazine (10.07 grams, 0.11 mole), dimethylformamide (140.87 grams) and sodium hydride (3.03 grams, 0.13 mole) were weighed into a reactor of the type described in Example 3. The reactor contents were stirred between 32°–50° C. for 2 hours 18 minutes (8280 s) in nitrogen atmosphere. Then methyl stearate (31.92 grams, 0.105 mole) was added to the reactor contents. The reactor contents were heated at a temperature between 140°–150° C. for 18 hours 23 minutes (66,180 s) giving a dark brown colored liquid. The reactor was fitted with a stillhead and its contents were subjected to distillation between 181°–258° C. and 34–51 mm mercury vacuum for 72 minutes (4320 s). The infrared Fourier Transform spectrum of the resulting brown solid showed the presence of unreacted methyl stearate, the sodium salt of stearic acid, and a secondary amide. The absorption bands at 1629 cm$^{-1}$ and 1417 cm$^{-1}$ were assigned to the asymmetrical and symmetrical stretch of the carboxylate ion of a salt, respectively. An absorption band at 1556 cm$^{-1}$ was assigned to the N—H bending vibration (Amide II band) of a secondary amide. A broad weak band between 3000 cm$^{-1}$–3310 cm$^{-1}$ was attributed to the NH stretching vibration of a secondary amide. The brown solid was dissolved in xylene for the corrosion inhibition tests.

EXAMPLE 8

Aminopyrazine (31.02 grams, 0.33 mole) and heptanoic anhydride (39.88 grams, 0.17 mole) were weighed into a reactor of the type described in Example 3. The reactor contents were stirred between 199°–242° C. for 26 hours 3 minutes (93,780 s). The resulting product was subjected to rotary evaporation under full vacuum between 82°–87° C. for 28 minutes (1680 s) giving a black solid. The infrared Fourier Transform spectrum of the black solid indicated the presence of methylene groups and a secondary amide. Absorption bands at 726 cm$^{-1}$, 1463 cm$^{-1}$, 2846 cm$^{-1}$ and 2931 cm$^{-1}$ support the presence of the methylene groups. Multiple bands between 3000 cm$^{-1}$–3003 cm$^{-1}$ were assigned to the NH stretching vibration of a secondary amide. The absorption band at 1682 cm$^{-1}$ was attributed to the carbonyl stretching vibration of a secondary amide. The band at 1549 cm$^{-1}$ was assigned to the N—H bending vibration of a secondary amide. The black solid was dissolved in ethanol for the corrosion inhibition tests.

EXAMPLE 9

Aminopyrazine (10 grams, 0.11 mole), dimethylformamide (142.34 grams), and sodium hydride (3.02 grams, 0.13 mole) were weighed into a reactor of the type described in Example 3. The reactor contents were stirred in a nitrogen atmosphere between 22°–33° C. for 2 hours 15 minutes (8100 s). Then heptanoic anhydride (12.83 grams, 0.05 mole) was added to the reactor. The reactor was heated at a temperature between 139°–152° C. for 22 hours 51 minutes (82,260 s). The resulting product was subjected to rotary evaporation under full vacuum at 85° C. for 30 minutes (1800 s) giving a brown solid. The brown solid wasmixed with acetone and filtered under full vacuum. The filtrant was a white solid while the filtrate was a brown liquid. The filtrate was rotary evaporated under full vacuum giving a brown solid. The infrared Fourier Transform spectrum of the brown solid indicated the presence of methylene groups and a secondary amide. The brown solid was dissolved in acetone for the corrosion inhibition tests.

EXAMPLE 10

Thermogravimetric analysis showed the acetone insoluble white solid from Example 9 lost only 6% weight at 403° C. The white solid was dissolved in water for the corrosion inhibition tests.

COMPARATIVE EXPERIMENT A

Tall oil fatty acid (102.25 grams, 0.36 mole) was neutralized with sodium hydroxide pellets while stirring to a pH of 8 at 196° C. over a period of 1 hour (3600 s). The infrared Fourier Transform spectrum of the resulting light brown taffy-like liquid indicated the presence of methylene groups, and unneutralized tall oil fatty acid. Absorption bands at 720 $cm^{-1}$, 1463 $cm^{-1}$, 2851 $cm^{-1}$ and 2924 $cm^{-1}$ supported the presence of methylene groups. The absorption band at 1702 $cm^{-1}$ was assigned to dimeric carboxylic carbonyl stretch of the unneutralized tall oil fatty acid. The light brown taffy-like liquid was dissolved in ethanol for the corrosion inhibition tests.

EXAMPLE 11

This example demonstrates the corrosion protection of Example 1 through 10 by the 80° C. (175° F.) batch wheel test procedure. The results are given in Table I.

TABLE I

| Test No. | Inhibitor Type | Concentration | Weight Loss (g) | Corrosion Rate MPY* | Percent Protection |
|---|---|---|---|---|---|
| A-1 | None | 0 | 0.1537 | 56.4 | 0 |
| A-2 | Ex. 1 | 100 ppm | 0.0122 | 4.4 | 92 |
| A-3 | Ex. 2 | 100 ppm | 0.0186 | 6.7 | 88 |
| A-4 | Corban A-163 | 100 ppm | 0.0246 | 9.0 | 84 |
| B-1 | None | 0 | 0.2024 | 77.1 | 0 |
| B-2 | Ex. 5 | 100 ppm | 0.0176 | 6.8 | 91 |
| B-3 | Ex. 6 | 100 ppm | 0.0524 | 20.4 | 74 |
| C-1 | None | 0 | 0.1847 | 69.9 | 0 |
| C-2 | Ex. 7 | 100 ppm | 0.0321 | 12.1 | 83 |
| D-1 | None | 0 | 0.1743 | 65.5 | 0 |
| D-2 | Ex. 3 | 100 ppm | 0.0058 | 2.2 | 97 |
| D-3 | Ex. 4 | 100 ppm | 0.0164 | 6.3 | 91 |
| D-4 | Ex. 8 | 100 ppm | 0.0616 | 22.9 | 65 |
| E-1 | None | 0 | 0.1812 | 69.6 | 0 |
| E-2 | Ex. 9 | 100 ppm | 0.0903 | 34.5 | 50 |
| E-3 | Ex. 10 | 100 ppm | 0.0883 | 33.8 | 51 |
| F-1 | None | 0 | 0.1990 | 74.4 | 0 |
| F-2 | Comp. Expt. A | 100 ppm | 0.1908 | 72.7 | 0 |

*milliinches per year

The data in Table I demonstrates that the inhibitors of this invention exhibit good corrosion protection under simulated down hole tests at 80° C. When the inhibitor is a salt of a carboxylic acid having at least 10 carbon atoms with an aminopyrazine compound or a pyrazineamide substituted with a hydrocarbyl group or a sulfur, halogen, nitro or hydroxyl substituted hydrocarbyl group having at least 10 carbon atoms, corrosion protection is much better than that exhibited by commercially available Corban A-163. The data in Table I also demonstrates that the sodium salt of a carboxylic acid is not the active ingredient of the products in Examples 4, 7 and 10 which is providing corrosion inhibition, since the sodium salt of tall oil fatty acid ( Comp. Expt. A) provides zero protection against corrosion. Therefore, the corrosion inhibitors or this invention are suitable for the protection of metal alloys against corrosion due to corrosive fluids produced in oil and gas well formations and harmful to said metal alloys at or below 80° C. In addition, the corrosion inhibitors of this invention are suitable for the corrosion protection of pipelines, storage tanks, pump, etc., that exist for the purpose of separating, and/or recovering gas from the produced fluids.

EXAMPLE 12

The following example demonstrates the performance of the inhibitors of this invention in a 350° F. (177° C.) wheel test. The concentrations and results are given in Table II.

TABLE II

| Test No. | Inhibitor Type | Concentration | Weight Loss (g) | Percent Protection |
|---|---|---|---|---|
| A-1 | None | 0 | 0.1082 | 0 |
| A-2 | Corban A-163 | 100 ppm | 0.0246 | 77 |
| A-3 | Textamine T5D | 100 ppm | 0.0485 | 55 |
| B-1 | None | 0 | 0.0838 | 0 |
| B-2 | Ex. 1 | 100 ppm | 0.0410 | 50 |
| C-1 | None | 0 | 0.0954 | 0 |
| C-2 | Ex. 2 | 50 ppm | 0.0340 | 65 |
| D-1 | None | 0 | 0.1022 | 0 |
| D-2 | Ex. 5 | 100 ppm | 0.0266 | 74 |

The above data shows that the inhibitors of this invention provide corrosion protection at 177° C. (350° F.) comparable to the corrosion protection provided by commercially available corrosion inhibitors.

EXAMPLE 13

2-Aminopyrazine (10.0129 grams, 0.0105 mole, 95.11 grams/mole), 29.7253 grams oleic acid (0.105 mole, 282.46 grams/mole) and 36.2477 grams xylene (0.3414 moles, 106.2 grams/mole) were weighed into 50 milliliter round bottom reactor equipped with a stirrer, thermometer, nitrogen purge system, Barrett trap and condenser. The resulting reaction mixture was heated between 25° and 189° C. for 58 minutes. At this time a small sample was removed and subjected to infrared spectroscopy. The infrared spectra showed a broad and intense band at 1630 $cm^{-1}$ and a band at 1409 $cm^{-1}$ which are due to the asymmetrical and symmetrical stretch of the carboxylate ion of a salt, respectively. The intense broad band between 3300 and 2500 $cm^{-1}$ is due to O—H stretching absorption of a carboxylic acid dimer. The intense band at 1712 $cm^{-1}$ is attributed to the dimeric carboxylic C=O stretch of a carboxylic acid. After an additional 38 hours between 189° and 205° C., the reactor contents were sampled. Infrared spectroscopy supported the presence of oleic acid dimer and no amide. The resultant product contained minor amounts of the salt of aminopyrazine and oleic acid.

I claim:

1. A process for preventing the corrosion of a metal composition in contact with a down hole well fluid which process comprises contacting the surface of said metal composition with an effective amount of, as a corrosion inhibitor, a composition resulting from reacting (A) at least one pyrazine compound represented by the formula

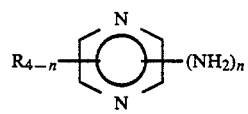

wherein each R is independently hydrogen, a hydrocarbyl group or a hydrocarbyloxy group, having from 1 to 20 carbon atoms: or a halogen atom, group and n has a value from 1 to 4;

(B) at least one carboxylic acid represented by the formulas

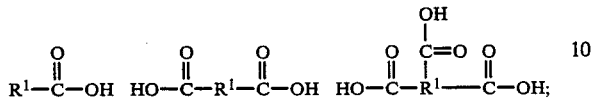

and wherein $R^1$ is an aliphatic or a cycloaliphatic group or a sulfur, halogen or hydroxyl substituted aliphatic or cycloaliphatic group having from 1 to 72 carbon atoms, and (C) optionally in the presence of sodium hydride; and wherein components (A) and (B) are present in quantities which provide a ratio of —CO— groups to —$NH_2$ or —NH— groups of from about 0.25:1 to about 1.2:1 and component (C) is present in quantities which provide a ratio of sodium hydride to —$NH_2$ or —NH— groups of from about 0:1 to about 1.5:1.

2. A process of claim 1 wherein said effective amount of corrosion inhibitor ranges from about one to about 2,000 ppm, based on the weight of said well fluid in contact with said metal composition.

3. A process of claim 2 wherein said corrosion inhibitor is contacted with a carrier liquid and subsequently with said well fluid.

4. A process of claim 1 wherein
  (i) components (A) and (B) are present in quantities which provide a ratio of —CO— groups to —$NH_2$ or —NH— groups of from about 0.75:1 to about 1.2:1; and
  (ii) component (C) is present in quantities which provide a mole ratio of sodium hydride to —$NH_2$ to —NH— groups of from about 0.75:1 to about 1.2:1.

5. A process of claim 4 wherein said effective amount of corrosion inhibitor ranges from one to about 2,000 ppm, based on the weight of said well fluid in contact with said metal composition.

6. A process of claim 5 wherein said corrosion inhibitor is contacted with a carrier liquid and subsequently with said well fluid.

7. A process of claim 4 wherein
  (i) components (A) and (B) are present in quantities which provide a ratio of —CO— groups to —$NH_2$ or —NH— groups of from about 0.9:1 to about 1.1:1;
  (ii) when the R group in component (A) is a hydrocarbyl or substituted hydrocarbyl group, said hydrocarbyl group has from 1 to 10 carbon atoms;
  (iii) when $R^1$ in component (B) is a hydrocarbyl group, said hydrocarbyl group has from 10 to 36 carbon atoms; and
  (iv) component (C) is present in quantities which provide a mole ratio of sodium hydride to —$NH_2$ to —NH— groups of from about 0.9:1 to about 1.2:1.

8. A process of claim 7 wherein said effective amount of corrosion inhibitor ranges from about one to about 2,000 ppm, based on the weight of said well fluid in contact with said metal composition.

9. A process of claim 8 wherein said corrosion inhibitor is contacted with a carrier liquid and subsequently with said well fluid.

10. A process of claim 1 wherein
  (i) when the R group in component (A) is a hydrocarbyl or substituted hydrocarbyl group, said hydrocarbyl group has from 1 to 4 carbon atoms; and
  (ii) when $R^1$ in component (B) is a hydrocarbyl group, said hydrocarbyl group has from 12 to 24 carbon atoms.

11. A process of claim 10 wherein said effective amount of corrosion inhibitor ranges from one to about 2,000 ppm, based on the weight of said well fluid in contact with said metal composition.

12. A process of claim 11 wherein said corrosion inhibitor is contacted with a carrier liquid and subsequently with said well fluid.

13. A process of claim 10 wherein
  (i) component (A) is pyrazinamine, 2,3-pyrazinediamine, 2,6-pyrazinediamine, or a combination thereof, and
  (ii) component (B) is dodecanoic acid, tetradecanoic acid, pentadecanoic acid, hexadecanoic acid, heptadecanoic acid, octadecanoic acid, tall oil fatty acid, $C_{21}$ dicarboxylic acid, or a combination thereof.

14. A process of claim 13 wherein said effective amount of corrosion inhibitor ranges from one to about 2,000 ppm, based on the weight of said well fluid in contact with said metal composition.

15. A process of claim 14 wherein said corrosion inhibitor is contacted with a carrier liquid and subsequently with said well fluid.

* * * * *